United States Patent [19]

Hall

[11] Patent Number: 4,626,208
[45] Date of Patent: Dec. 2, 1986

[54] POSITIONING JIG FOR EDGEWISE BRACKET

[75] Inventor: Arthur B. Hall, LaPorte, Ind.

[73] Assignee: TP Orthodontics, Inc., Westville, Ind.

[21] Appl. No.: 766,873

[22] Filed: Aug. 16, 1985

[51] Int. Cl.⁴ .............................................. A61C 7/00
[52] U.S. Cl. ................................................... 433/3
[58] Field of Search ....................................... 433/2, 3

[56] References Cited

U.S. PATENT DOCUMENTS 4,523,908  1/1985  Drisaldi et al. ..................... 433/3

OTHER PUBLICATIONS

T. P. Labs. Inc. Catalog 906 (1981) p. 10.

Primary Examiner—Robert Peshock
Attorney, Agent, or Firm—Lloyd L. Zickert

[57] ABSTRACT

A positioning jig for an edgewise bracket having a lingually disposed vertical slot or opening to position the bracket on a tooth when bonding the bracket to the tooth. The jig is disposable and mounted on the bracket to be handled as a unit during the bonding procedure and thereafter removable from the bracket once the bonding material has cured. Indicia is provided on the jig and the bracket to identify the tooth on which the bracket is to be mounted and the spacing of the archwire slot from the occlusal or incisal edge of the tooth.

8 Claims, 7 Drawing Figures

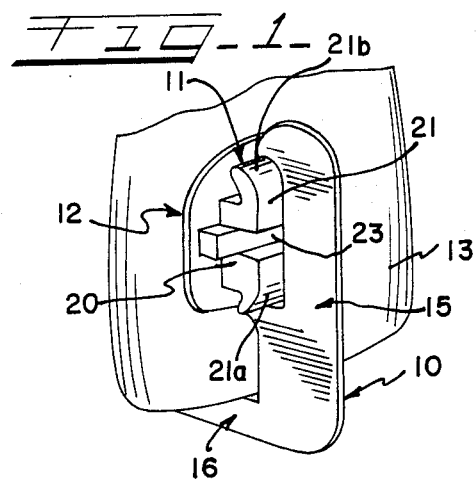
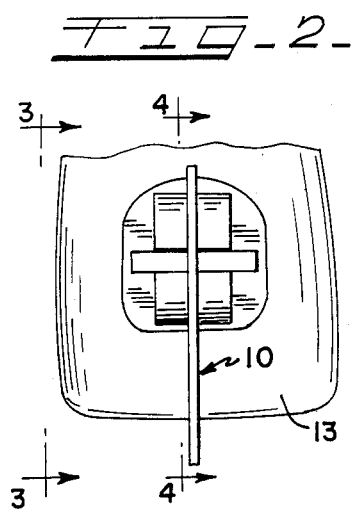
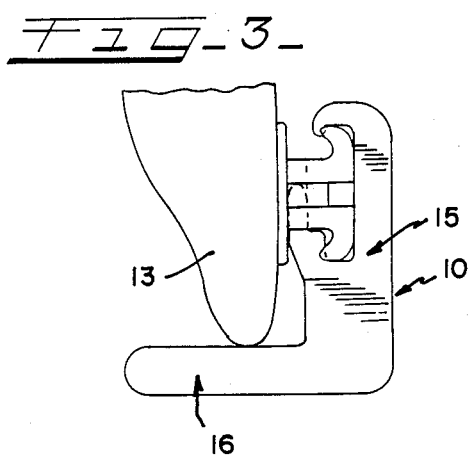
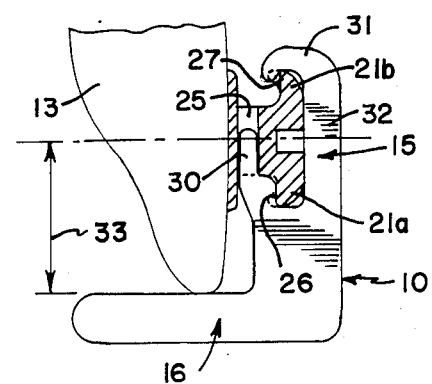
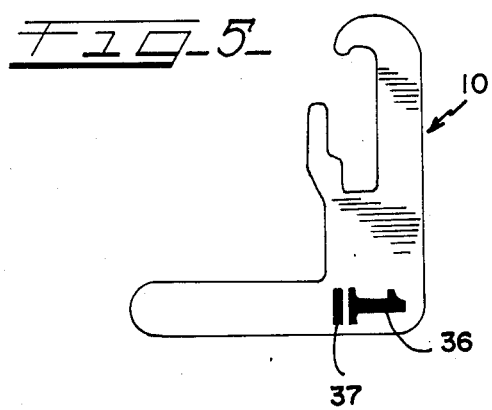
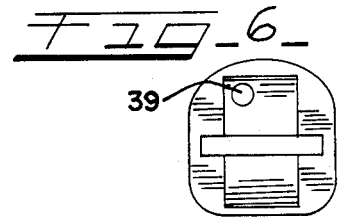
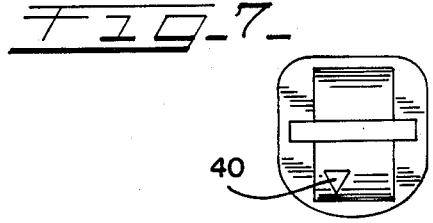

POSITIONING JIG FOR EDGEWISE BRACKET

This invention relates in general to a positioning jig for an egewise bracket, and more particularly to a disposable positioning jig provided in combination with an edgewise bracket for positioning the bracket archwire slot a given distance from the occlusal or incisal edge of a tooth, and still more particularly to an identification system for indicating the tooth on which the bracket is to be mounted and the distance the archwire slot is to be disposed from the occlusal or incisal edge of the tooth.

BACKGROUND OF THE INVENTION

Heretofore, there have been available a variety of positoning jigs or gauges for assisting in the positioning of a bracket on a tooth. Not only have these positioning jigs been developed for edgewise brackets but also for light-wire brackets. Some of the jigs have also been disposable.

The positioning jig of the present invention is an improvement over heretofore known jigs for edgewise brackets in that it simplifies the bracket mounting procedure and positively identifies the location for the bracket. Further, the jig of the invention simplifies the packaging of the bracket particularly because the brackets and the jigs can be mounted on a surface with the front of the bracket facing upwardly so that indicia on the bracket and jig is visible for identifying bracket location and so that the bracket and jig may be easily grasped with a suitable tool for transfer to a tooth in the mouth of a patient.

SUMMARY OF THE INVENTION

The jig of the present invention is particularly adaptable for use with single tie-wing edgewise brackets having a lingually disposed vertical slot or opening. The jig includes a bracket engaging portion and a gauge arm. The bracket engaging portion includes a first finger for engaging the slot or opening from the occlusal end and a second finger for engaging the buccal surface and over the gingival edge of the bracket tie wing. The bracket engaging portion extends vertically when oriented adjacent a tooth, and the gauge arm projects substantially at right angles to the bracket engaging portion for abutting against the occlusal or incisal edge of a tooth. Color coding of the jig indicates the spacing that will be defined between the occlusal or incisal edge and the archwire slot. Generally, there will be three different colors denoting spacings of 3½ mm., 4 mm., or 4½ mm., although any number of colors and spacings may be provided. Additionally, indicia will be provided on the jig and on the labial of the bracket to identify the tooth location. Once the bonding procedure has been completed, the jig may be suitably removed.

It is therefore an object of the present invention to provide a new and improved positioning jig for an edgewise bracket to facilitate the orientation and positioning of the bracket on a tooth.

A further object of the present invention is in the provision of a new and improved positioning jig for an edgewise bracket that simplifies the positioning of the bracket on a tooth, and an identification system including color coding and indicia that precisely indicates the bracket location.

A still further object of the present invention is to provide a new and improved disposable positioning jig that is provided in combination with a bondable bracket to simplify the positioning of the bracket on a tooth and determination of bracket location.

Other objects, features and advantages of the invention will be apparent from the following detailed disclosure, taken in conjunction with the accompanying sheet of drawings, wherein like reference numerals refer to like parts, in which:

BRIEF DESCRIPTION OF THE DRAWINGS

FIG. 1 is a perspective view of the positioning jig of the present invention in combination with an edgewise bracket and demonstrating the manner in which the jig facilitates the positioning of the bracket on a tooth;

FIG. 2 is a front elevational view of the bracket and positioning jig shown in FIG. 1 and also illustrating the positioning function of the jig;

FIG. 3 is a side elevational view of the jig and bracket and illustrating the manner in which the jig positions the bracket on a tooth and taken along line 3—3 of FIG. 2;

FIG. 4 is a vertical sectional view taken substantially along line 4—4 of FIG. 2;

FIG. 5 is a side elevational view of a positioning jig removed from a bracket and also having indicia for indicating the location;

FIG. 6 is a front elevational view of a bracket without a positioning jig and indicating one type of indicia applied to the bracket for identifying tooth location; and FIG. 7 is a view similar to FIG. 6 and illustrating another type of indicia applied to the bracket for identifying tooth location.

DESCRIPTION OF THE INVENTION

Referring now to the drawings and particularly to FIG. 1, the positioning jig of the invention, generally indicated by the numeral 10, is illustrated in mounted relation with an edgewise bracket 11 on a base or bonding pad 12 and in position on a tooth 13 to demonstrate the positioning capability of the jig. While the illustrated tooth 13 depicts an upper incisor, it will be appreciated that the bracket positioning jig of the present invention is equally useful for orienting and positioning brackets on other teeth.

The bracket positioning jig of the invention is particularly suitable for use with an edgewise bracket having a single tie wing and a lingually disposed vertical slot or opening usable for receiving pins or spring tails or ligating wire. The jig is disposed generally perpendicular to the horizontal axis of the bracket and generally perpendicular to the horizontal archwire slot where the archwire slot is parallel to the horizontal axis. Further, the jig is positioned centrally between the opposing mesial and distal edges of the bracket so as to facilitate the central positioning of a bracket on a tooth when centrally locating the jig between the mesial and distal edges of the tooth.

The jig includes a bracket engaging and supporting portion 15, defined to engage and support the bracket, which extends vertically when the bracket is positioned within the mouth on a tooth, and a gauge arm 16 projecting lingually and extending generally perpendicular to the bracket supporting and engaging portion 15, as particularly seen in FIGS. 3 and 4.

The disposition of the gauge arm 16 as it relates to the bracket further facilitates the packaging of the combination bracket and jig in that the gauge arm may be depressed vertically into a styrofoam or the like panel until the bonding surface of the bracket engages the surface of the panel. This holds it at a given oriented position on the panel. Thereafter, when the orthodontist is desirous of mounting a bracket, it is easy to grasp the jig with a suitable tool and transfer it from the styrofoam panel to an oriented position on a tooth. Also, as will be more clearly hereafter disclosed, the identification for the bracket to indicate its location is readily visible while the bracket and jig is mounted on the styrofoam panel.

The bracket 11 includes a base portion 20 and a tie or ligating wing 21 extending buccolabially from the base. Tie wing 21 includes incisal and gingival tie wing ears 21a and 21b. A horizontally opening archwire slot 23 is formed at the buccolabial of the tie wings and which would receive a suitable archwire. While the slot is rectangular in cross section, it could receive either a round or rectangular archwire. The slot 23 is parallel to the horizontal axis of the bracket, although it may be appreciated that the slot may be angularly related to the horizontal axis, depending upon the type of correcting forces desired. The lingual surface of the base portion is suitably secured to the bonding pad 12.

The base portion 20 of the bracket includes a vertical slot 25 at the lingual end disposed centrally between the mesial and distal edges of the bracket. Such a slot is capable of receiving a pin, a spring tail, a ligating wire, or the like. The slot 25 is in the form of an opening when closed on the backside by the bonding pad. It should be appreciated that the jig of the invention can equally well be used with a one-piece bracket such as a cast bracket having a lingual bonding surface and a lingually disposed vertical opening equal to the opening or slot 25 which is used by the jig for connecting the jig to the bracket and for orienting the jig relative to the bracket.

The bracket positioning jig 10 is preferably made of inexpensive plastic. It could be molded, or suitably cut or stamped from a sheet of plastic. While the jig is made of a plastic that is somewhat rigid, it has sufficient flexibility to facilitate the mounting of the jig onto the bracket. When molded, it could have oval or round cross-sectional portions. The bracket engaging and supporting portion 15 includes a first finger 30 adapted to be frictionally received in the bracket opening or slot 25 from the incisal end, as seen particularly in FIGS. 3 and 4. The lower end of the first finger is wider labiolingually and connected to the bracket supporting portion 15. Finger 30 is interconnected to a second finger 31 by an arm 32, whereby the second finger is in generally opposed relation to the first finger and spaced so that it can frictionally engage the gingival tie wing ear 21b, as seen in FIG. 4. Notches 26 and 27 are respectively provided on the lingual edges of the tie wing ears 21a and 21b for receiving a part of the fingers 30 and 31 and providing additional orientation of the jig on the bracket.

The fingers 30 and 31 and the arm 32 of the bracket engaging and supporting portion 15 coact with the gauge arm 16 to define the distance between the archwire slot and the gingival edge of the gauge arm, as illustrated by the arrow 33 in FIG. 4. It is this distance that is chosen by the orthodontist for the spacing of the archwire slot relative to the incisal or occlusal edge of the tooth. The jigs are made in several sizes to vary this distance and color coded to immediately convey to the orthodontist the spacing distance. Thus, the orthodontist picks a jig and bracket unit with a colored jig matching the distance desired for spacing of the archwire slot.

Since brackets are usually designed for given teeth, it is important to identify the bracket prior to the mounting procedure. The present invention also includes an identification system for determining bracket location. This system includes indicia on both the jig and the bracket, as seen particularly in FIGS. 5 to 7. Since teeth are usually identified by a number, the identification system includes the application of a numerical legend 36 to one side of the bracket jig at the location of the portion of the jig that will be exposed when packaged on a styrofoam panel, as particularly seen in FIG. 5. Secondly, inasmuch as the numbers apply to teeth in both the upper and lower arches, a bar symbol 37 coacts with the numerical legend 36 to indicate whether the bracket is designed for an upper or lower tooth. When the bar symbol 37 is disposed below the numerical legend, as shown in FIG. 5, it indicates that the bracket is for a tooth in the upper arch. When the bracket is designed for a tooth in the lower arch, the bar symbol is placed above the numerical symbol.

Since the usual numbering system is for right or left teeth, a chosen symbol is applied to the labial of the bracket in a position to indicate whether the bracket is for a right or left tooth. The symbol is applied to the tie wing and particularly to the distal side of the tie wing indicating the side or edge to be distal in the mouth. Further, the symbols on the bracket additionally indicate whether the bracket is for an upper or lower arch. Thus, the symbols as positioned relative to the jig indicate in which quadrant of the mouth the bracket is to be located. The round or circular symbol 39 shown in FIG. 6 may, for example, indicate the bracket is for the maxillary arch, while the triangular symbol 40 in FIG. 7 would indicate the bracket is for the mandibular arch. Further, the symbol is preferably placed at the distogingival corner of the bracket so as to provide a check as to whether the bracket is properly disposed on the positioning jig. Accordingly, the exact bracket location can be determined visually by the indicia on the jig and the bracket and, as above explained, the archwire slot spacing is indicated by the color coding of the jig.

While the procedure for handling the bracket and jig of the invention is readily understandable from the above description, it will be appreciated that the tooth and bonding surface of the bracket is first prepared for bonding and then the bracket and jig would be brought to the tooth on which it is to be mounted and oriented on the tooth centrally between the mesial and distal edges of the tooth and so that the gauge arm engages the incisal or occlusal edges of the tooth, as illustrated in the drawings.

After the bonding material has sufficiently cured or set, the positioning jig would then be removed from the bracket. This may be accomplished by grasping the jig in the area of the gauge arm by a suitable tool and twisting it sideways to disengage the gingival portion of the jig. Thereafter, it is a simple matter to pull the jig incisally away from the bracket and dispose of it.

Accordingly, it is seen in view of the foregoing that the bracket positioning jig of the invention facilitates the identification of brackets and the mounting of brackets on teeth and coacts with indicia on the brackets for indicating bracket location to reduce the time spent by the orthodontist in properly placing and bonding the bracket to a tooth.

It will be understood that modifications and variations may be effected without departing from the scope of the novel concepts of the present invention, but it is understood that this application is to be limited only by the scope of the appended claims.

I claim:

1. A disposable positioning jig in combination with a single tie-wing edgewise bracket having a lingually disposed vertical slot or opening to position the bracket on a tooth for bonding, wherein the bracket includes a base having a lingual bonding surface and a centrally disposed lingual vertical slot or opening, and a tie wing extending buccolabially from the base, said tie wing including gingival and incisal tie wing ears and having a horizontal labiobuccally opening archwire slot, said jig including a vertical bracket engaging portion having a first finger frictionally fitting within the vertical slot or opening from the occlusal end, a second finger interconnected with the first finger and frictionally engaging over and around the gingival edge of the bracket tie wing, and a gauge arm extending substantially at right angles to said bracket engaging portion for contacting the occlusal of the tooth on which the bracket is mounted to space the archwire slot a predetermined distance from the occlusal, the thickness of said jig being substantially less than the mesiodistal dimension of said tie wing.

2. The combination of claim 1, which further includes means for identifying the tooth on which the bracket is to be mounted and the spacing of the archwire slot from the occlusal.

3. The combination of claim 1, wherein said identifying means includes a numeral on the jig with a line disposed above or below the numeral to identify the tooth and arch location for the bracket.

4. The combination of claim 3, wherein said identifying means further includes a symbol on the buccolabial face of the tie wing defining the arch and quadrant location.

5. The combination of claim 4, wherein said identifying means further includes a color to define the spacing of the archwire slot from the occlusal.

6. The combination of claim 1, wherein said tie wing ears include notches for receiving the jig fingers.

7. A positioning jig for an edgewise bracket having a single tie wing extending from a base and a lingually disposed vertical slot or opening for mounting the bracket on a tooth, said jig comprising a planar body having a bracket supporting portion and a gauge portion, the bracket supporting portion including a first finger for frictionally engaging and extending into said slot or opening at the occlusal end and a second finger interconnected to the first finger and frictionally engaging over and around the gingival edge of the tie wing, and the gauge portion including an arm extending lingually and generally perpendicular to said bracket supporting portion to abut the occlusal or incisal edge of the tooth on which it is to be mounted, the thickness of said jig being substantially less than the width of the bracket tie wing.

8. The jig of claim 7, wherein the bracket tie wings include notches for receiving the jig fingers.

* * * * *